United States Patent [19]
Babcock et al.

[11] 3,980,638
[45] Sept. 14, 1976

[54] TESTOSTERONE DERIVATIVES

[75] Inventors: John C. Babcock; J. Allan Campbell, both of Kalamazoo, Mich.

[73] Assignee: The Upjohn Company, Kalamazoo, Mich.

[22] Filed: Sept. 20, 1974

[21] Appl. No.: 507,690

[52] U.S. Cl. .................... 260/239.55 R; 260/397.4; 260/239.55 R; 424/241
[51] Int. Cl.² ......................................... C07J 17/00
[58] Field of Search ......./Machine Searched Steroids; 260/239.55 R, 397.4

[56] References Cited
UNITED STATES PATENTS

| | | |
|---|---|---|
| 3,135,743 | 6/1964 | Clinton et al. ................. 260/239.55 |
| 3,296,255 | 1/1967 | Clinton et al. ................. 260/239.55 |
| 3,562,260 | 2/1971 | De Ruggieri et al. .......... 260/239.55 |
| 3,732,209 | 5/1973 | Fahrenholtz et al. ............ 260/239.5 |

*Primary Examiner*—Elbert L. Roberts
*Attorney, Agent, or Firm*—Bruce Stein; Willard L. Cheesman

[57] ABSTRACT

Novel testosterone 17-ether 2,3-isoxazole and 2-cyano derivatives are disclosed as useful steroid enzyme inhibitors and for other pharmaceutical purposes.

5 Claims, No Drawings

TESTOSTERONE DERIVATIVES

BACKGROUND OF THE INVENTION

The effects of several natural and synthetic steroids as inhibitors on the activity of $\Delta^5$-$3\beta$-hydroxysteroid dehydrogenase have been disclosed, including that of certain 2-cyano-$\Delta^5$ androstenes in Biochem. Biophys. Acta E 315, 233 (1973). The chemical procedures are known whereby 3-keto steroids can be converted to $2\alpha$-cyano-3-ketones via the [2,3-d]isoxazoles, and the substance "cyanoketone" has been described as a reference standard for enzyme inhibition, in J. Med. Chem. 6 1 (1963).

BRIEF STATEMENT OF THE INVENTION

The compounds of this invention have the following structural formulae:

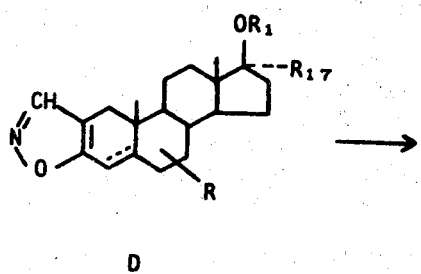 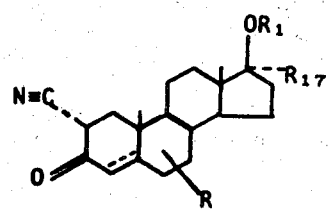

D  E wherein $R_{17}$ = hydrogen or alkyl of 1 to 5 carbon atoms, alkenyl of 2 to 5 carbon atoms and alkynyl of 2 to 5 carbon atoms, preferably hydrogen, methyl, ethynyl and methylethynyl, $R_1$ = lower alkyl of 1 to 5 carbon atoms, cycloalkyl of 3 to 12 carbon atoms and aralkyl of 7 to 12 carbon atoms, preferably methyl, cyclopentyl and benzyl, R = hydrogen and $6\alpha,7\alpha$, and $7\beta$-monomethyl.

The compounds of this invention also include the corresponding 19-nor derivatives.

The above class of compounds are useful steroid enzyme inhibitors and the compounds have potential therapeutic utility in the treatment of benign prostatic hypertrophy, hirsutism, acne and steroid hormone-dependent tumors. They can also be used as antifertility agents in human males and females and in birds and domestic animals.

The pharmaceutical compositions of the present invention are presented for administration to humans and animals in dosage forms such as tablets, capsules, pills, powders, granules, sterile parenteral solutions or suspensions, oral solutions or suspensions, and oil-water emulsions containing suitable quantities of compounds of formula D or E. Suitable diluents, carriers and coating materials for the active drugs are, carbohydrates (lactose or manitose) proteins, lipids, calcium phosphate, corn starch stearic acid, calcium stearate, methyl cellulose and the like. For preparing solutions and suspensions, water, propylene glycol, oils e.g. coconut oil, sesame oil, safflower oil, cottonseed oil, and peanut oil may be used. Sweetening, coloring and flavoring agents may be added. For animals besides the above mentioned dosage forms food premixes with starch, grains, fishmeal, flour and the like can be prepared.

The dosage of compounds of formula D and E depends on the route of administration, age, weight, and condition of the patient. The daily dose of 10 to 300 mg. in single or divided doses embraces effective range of treatment.

The compounds of this invention can be prepared in accordance with the following series of reaction steps:

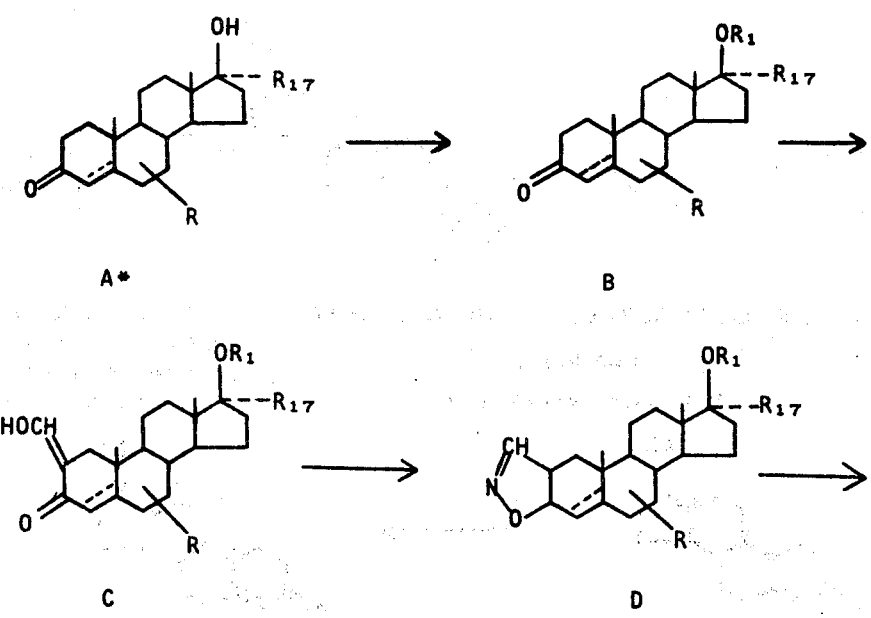

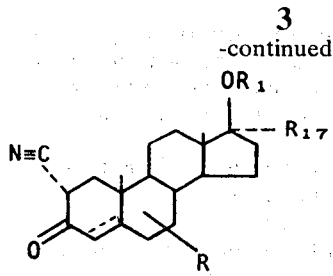

E

*The broken line between C-4 and C-5 represents alternatively a Δ⁴ double bond or 5 αH.

The sequence in the synthesis of the products of this invention consists in preparing the appropriate 17-alkyl ether B, some of which are known, from the precursor alcohol A, preparing the 2-formyl derivatives thereof (C), the isoxazole (D), and the 2α-carbonitrile(E). In the above sequence, testosterone and 5α-dihydrotestosterone (A, R=R$_{17}$=H) are illustrative of the starting materials. However, the process is equally applicable for the analogous 19-nor compounds, for 17-alkyl, alkenyl, and alkynyl substituted steroids, and for the corresponding known steroids which in addition contain a 6α,7α, or 7β-monomethyl substituent (R=6α,7α, and 7β-CH$_3$).

Preferred products are D and E derived from the 17-methyl ethers of: testosterone, 17-methyl-testosterone, 19-nortestosterone, 17-methyl-19-nortestosterone, 5α-dihydrotestosterone, 17-methyl-5α-dihydrotestosterone, 19-nor-5α-dihydrotestosterone (17β-hydroxyestran-3-one) and 19-nor-17-methyl-5α-dihydrotestosterone. Likewise the 6α,7α and 7β methyl analogs of D and E compounds can be prepared and used for the above purposes.

A solution of 50 g. of testosterone in 500 ml. of dimethylformamide was cooled to 5° C in an ice bath and 58 g. of silver oxide and 85 ml. of N,N-diisopropylethylamine was added. The mixture was stirred and 62 ml. (142 g.) of methyl iodide was added in a slow stream. The temperature was about 5° C. Stirring was continued as the ice bath was allowed to melt and come to room temperature. After 18 hours 2 liters of ether was added and the mixture was filtered through a bed of celite to remove the inorganic salts. The filtrate was washed with water, dilute hydrochloric acid, again with water, dried (Na$_2$SO$_4$), filtered, and concentrated. The product was chromatographed through silica gel and recrystallized from acetone-Skellysolve B, yield m.p. 21.2 g. m.p. 128°–129° λnm$^{alc}$ 241 nm ε = 16,550, second crop from methanol, yield 12.7 g. m.p. 125°–128° [Lit. JACS 80 2584 (1958) m.p. 127°–127.5°].

Using this procedure the methyl ethers of the Δ$_4$ 3-ketones of formula A can be prepared. When other iodides are substituted for methyl iodide other 17-methyl ethers will be produced. When C$_{17}$ is not H reaction times can be extended, and additional quantities of reagents can be added to improve the conversion.

There are thus produced the methyl, ethyl propyl, cyclopentyl, benzyl and other ethers of testosterone, 17-methyl-, 17-ethinyl-, and 17-propinyl-testosterone, 19-nortestosterone, 17-methyl-, 17-ethinyl, and 17-propinyl-19-nortestosterone and the corresponding 6α,7α, and 7β-methyl analogs thereof.

EXAMPLE 2

Dihydrotestosterone methyl ether

DETAILED DESCRIPTION OF THE INVENTION

EXAMPLE 1

Testosterone Methyl Ether

In the above reaction the 3-keto group can be protected in known manner. The etherification reaction can be carried out in known manner with etherification agents and conditions for introducing the desired R$_1$ substituent. The etherification can be carried out on the crude product of the first step, or the protected compound can be purified before etherification. The 3-keto group can be regenerated in known manner.

To a warm solution of 33 g. of 5α-dihydrotestosterone in 60 ml. of chloroform was added 250 ml. of ethylene glycol and 1.5 g. of p-toluene sulfonic acid. The solution was heated on the steam bath and after about 3 min. the solution became thick with crystals of ketal. The chloroform was evaporated on the rotary evaporator by heating with steam. The mixture was cooled to about 35° C., filtered and washed with a little fresh glycol and water. After drying at 50° C. under vacuum 49 g. (98%) of ketal was obtained m.p. 171°–174°.

Without further purification it was methylated as described above for testosterone. The crude product may be chromatographed to purify it, but in this case, was triturated with 50 ml. of cold acetone to give 44.5 g. (88%) of the methyl ether m.p. 134°–136°.

The product was dissolved in 40 ml. of methylene chloride and 200 ml. of acetone and 2 ml. of 1N aqueous perchloric acid was added. The solution was heated near the boiling point for 2 hours then the methylene chloride was boiled off and acetone and water was added (also at the b.p.) to give 200 ml. of a turbid solution. The crystals that formed on cooling were filtered, washed with water and recrystallized from 95% ethanol, yield 31.6 g. m.p. 125°–126°. An additional 3 g. was obtained from the mother liquors. [Lit. m.p. 125°–126°, J. Chem. Soc. C 421 (1968)].

When this procedure is applied to the compounds of generic formula A (item 9) the corresponding methyl ethers B are produced. When $R_{17}$ is other than H the reaction times and amounts of reagents may be increased to obtain better yields.

There are thus produced the methyl, ethyl, propyl, cyclopentyl, benzyl and other ethers of 5α-dihydrotestosterone, 17-methyl-, 17-ethinyl-, and 17-propinyl-5α-dihydrotestosterone, 19-nor-5α-dihydrotestosterone, 17-methyl-, 17-ethinyl-, and 17-propinyl-19-nor-5α-dihydrotestosterone and the corresponding 6α-, 7α-, and 7β-methyl analogs thereof.

EXAMPLE 3

17β-Methoxy-2-hydroxymethylene-5α-anydrostan-3-one

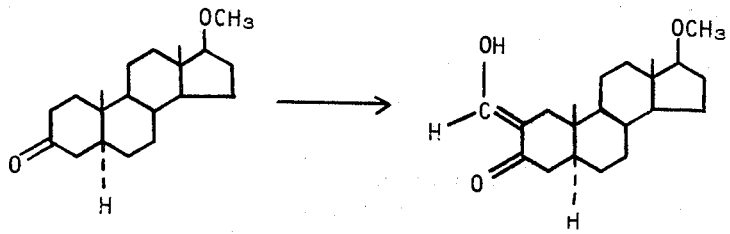

To a stirred mixture of 9 g. of sodium hydride (58% dispersion in mineral oil-the oil was removed by washing with benzene) in 350 ml. of benzene was added 30 g. 17β-methoxy-5α-androstan-3-one and 38 ml. of ethyl formate. After about 1 hour the temperature reached 40° so the reaction mixture was cooled to 30° with a cold water bath. After 4 hours the mixture was diluted with ether and water and acidified with dilute hydrochloric acid. The organic phase was separated, washed well with water, dried and concentrated to a yellow amorphous solid, yield 33 g. Two grams were reprecipitated from acetone m.p. 178°–182° (changed from amorphous solid to crystals before melting). $\alpha max^{alc}$ 282 nm $\epsilon = 9,000$.

Anal. Calcd for $C_{21}H_{32}O_3$: C, 75.86; H, 9.70. Found: C, 75.71; H, 9.67.

Application of this reaction to other compounds of formula B produce compounds of formula C.

Thus, substituting the compounds found in Example 2 as starting material in Example 3, there are produced the corresponding 2-hydroxymethyl compounds of formula C.

EXAMPLE 4

2-Hydroxymethylene-17β-methoxyandrost-4-en-3-one

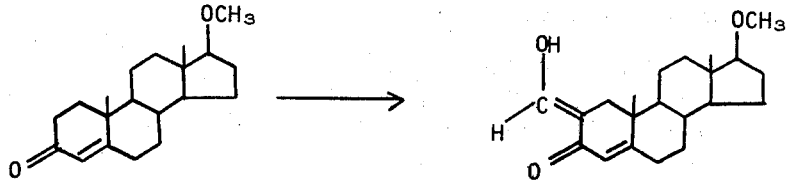

Under the conditions described above except reaction time extended to 4 days, 20 g. of testosterone methyl ether yielded the 2-hydroxymethylene compound, 10.6 g. (from acetone-Skellysolve B). An analytical sample recrystallized from ethyl acetate had m.p. 130–134°, $\lambda max^{alc}$ 219 nm ($\epsilon = 5,800$), 250 ($\epsilon = 12,250$) 308 ($\epsilon = 5,950$).

Application of this reaction to compounds of formula B yields corresponding compounds of formula C.

Thus, substituting the compounds found in Example 1 as starting material in Example 4, there are produced the corresponding 2-hydroxymethylene compounds of formula C.

EXAMPLE 5

17β-Methoxy-5α-androst-2-ene(2,3-d)isoxazole

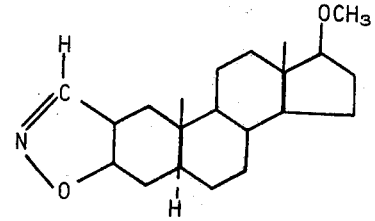

To a warm slurry of 30 g. of 2-hydroxymethylene-17β-methoxy-5α-androsten-3-one in 500 ml. of 95% ethanol was added 6.6 g. of hydroxylamine hydrochloride in 7 ml. of water. The mixture was refluxed ½ hour and concentrated to about 200 ml. and 50 ml. of water was added. The mixture was chilled and the precipitated isoxazole filtered and washed with water and a little Skellysolve B. It was dissolved in methylene chloride and filtered through a bed of silica gel and recrystallized from 95% ethanol, to give 16.7 g. of the isoxazole m.p. 131°–133°.

NMR: (CDCl$_3$) δ 0.75 (s, C-18), 0.78 (s, C-19), 3.29 (t, J = 8 C-17), 3.38 (s, —OCH$_3$), 8.03 (s, isoxazol C—H).

This procedure is applicable to compounds of formula C to give compounds of formula D. Alternatively the reaction can be buffered by the addition of sodium acetate or pyridine.

Thus, substituting the 2-hydroxymethylene analogs obtained in Example 3, there are produced the corresponding isoxazoles of formula D.

EXAMPLE 6

17β-Methoxyandrosta-2,4-dieno(2,3-d)isoxazole

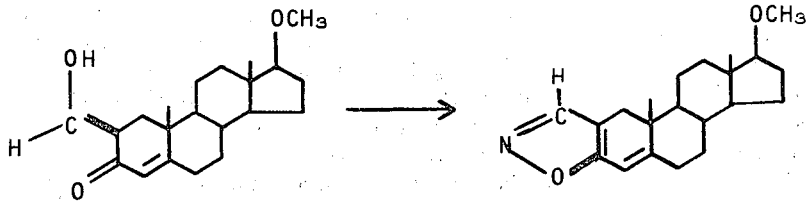

A mixture of 10 g. of 2-hydroxymethylene-17β-methoxyandrost-4-en-3-one in 200 ml. of 95% ethanol and 2.21 g. of hydroxylamine hydrochloride in 2 ml. of water was refluxed for ½ hour, concentrated to about 75 ml. and the isoxazole was precipitated with water, and recrystallized from aqueous methanol, yield 8.55 g., m.p. 107°–110°, λmax$^{alc}$ 284 nm ε = 11,400. m.s. m/e 327 (M+) 312, 280, 254, 147. NMR (CDCl$_3$) δ 0.80 (s, C-18), 1.01 (s, C-19), 3.24 (t J = 8, C-17) 3.32 (OCH$_3$), 6.15 (s C-4), 7.98 (s, isoxazole C-H).

Anal. Calcd for C$_{21}$H$_{30}$O$_2$: C, 76.32; H, 9.15. Found: C, 76.47; H, 8.78.

This procedure is applicable to compounds of formula C to give compounds of formula D. Alternatively the reaction can be buffered by the addition of sodium acetate or pyridine.

Thus, substituting the 2-hydroxymethylene analogs obtained in Example 4, there are produced the corresponding isoxazoles of formula D.

EXAMPLE 7

17β-Methoxy-3-oxo-5α-androstane-2α-carbonitrile

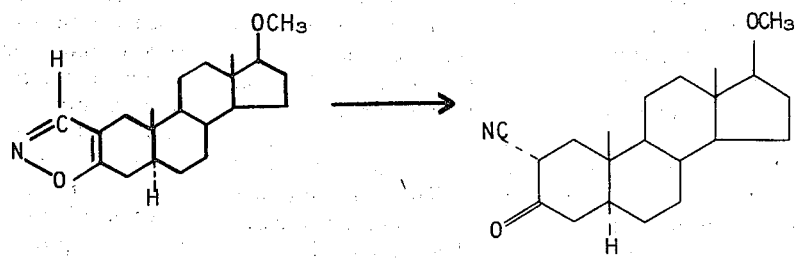

To a solution of 14 g. of 17β-methoxy-5α-androst-2ene(2,3-d)-isoxazole, in 100 ml. of tetrahydrofuran (purified by percolating through alumina) was added 5 g. of powdered sodium methoxide. After 1 ¼ hours the reaction mixture was diluted with water, acidified, extracted with ether and recrystallized twice from 95% ethanol to give 10.1 g. of 2-nitrile m.p. 192°–194°.

IR: (nujol mull) 3180 (OH), 2200 (C ≡ N), 1745, 1740 (very weak), 1635 (C=C, strong).

NMR (CDCl$_3$): (a mixture of keto and enol forms). δ 0.73 (C-19), 1.07 (C-18 keto form), 0.72 (C-18 enol form), 3.22 (m, C-12), 3.30 (OCH$_3$), 3.7 (m weak and erased with D$_2$O, C-12).

Anal. Calcd for C$_{21}$H$_{31}$NO$_2$: C, 76.55; H, 9.48; N, 4.25. Found: C, 77.08; H, 9.95; N, 4.45.

This procedure, applied to compounds of formula D, affords compounds of formula E.

Thus, substituting the isoxazoles obtained in Example 5, there are produced the corresponding 2α-carbonitriles of formula E.

EXAMPLE 8

17β-Methoxy-3-oxoandrost-4-ene-2α-carbonitrile

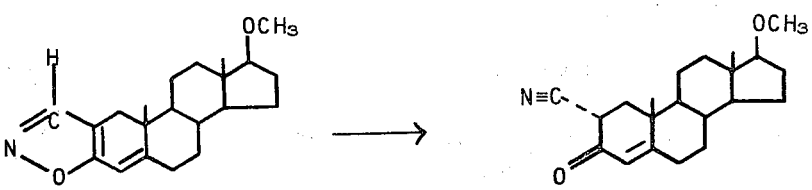

To a solution of 7 g. of 17β-methoxyandrosta-2,4-diene(2,3-d)isoxazole in 50 ml. of tetrahydrofuran (purified) was added 2.5 g. of sodium methoxide powder. After 1 hour reaction time water and ice were added and the solution acidified with 6N hydrochloric acid. The precipitated nitrile was filtered, washed, dried and recrystallized from acetone-Skellysolve B to give 5.5 g. of the nitrile m.p. 145°–150°, λmax$^{alc}$ 242 nm ε = 15,250 m/s, m/e = 327 (M+), 295, 254, 199, 147. IR, 2250 (C≡N), 1695, 1985 (C=O), 1620 (C=C).

Anal. Calcd for $C_{21}H_{29}NO_2$: C, 77.02; H, 8.93; N, 4.28. Found: C, 77.29; H, 8.93; N, 4.10.

This reaction when applied to compounds of structure D yields compounds of structure E.

Thus, substituting the isoxazoles obtained in Example 6, there are produced the corresponding 2α-carbonitriles of formula E.

We claim:

1. A compound of the group consisting of

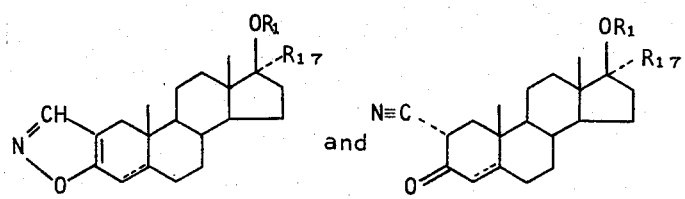

where the broken line in ring A denotes a double bond or the 5α structure, $R_1$ = lower alkyl of 1 to 5 carbon atoms, cycloalkyl of 3 to 12 carbon atoms and aralkyl of 7 to 12 carbon atoms, $R_{17}$ = hydrogen or alkyl of 1 to 5 carbon atoms, alkenyl of 2 to 5 carbon atoms.

2. A compound according to claim 1 of the formula:

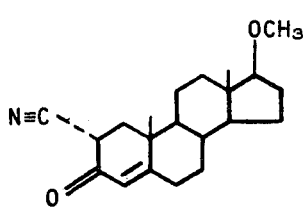

3. A compound according to claim 1 of the formula:

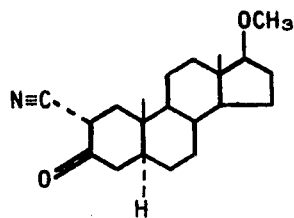

4. A compound according to claim 1 of the formula

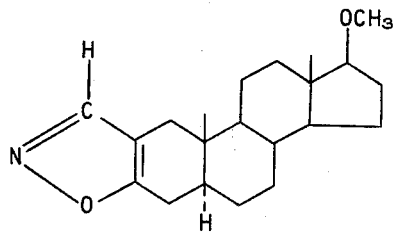

5. A compound according to claim 1 of the formula

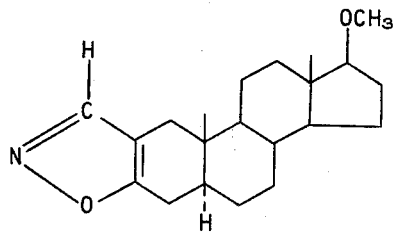

* * * * *